United States Patent [19]

Cooper

[11] Patent Number: 4,587,364
[45] Date of Patent: May 6, 1986

[54] HYDROFORMYLATION PROCESS EMPLOYING UNMODIFIED OSMIUM-COBALT CATALYST

[75] Inventor: James L. Cooper, Longview, Tex.

[73] Assignee: Eastman Kodak Company, Rochester, N.Y.

[21] Appl. No.: 612,210

[22] Filed: May 21, 1984

[51] Int. Cl.$^4$ .............................................. C07C 45/50
[52] U.S. Cl. ................................................ 568/451
[58] Field of Search ......................................... 568/451

[56] References Cited

U.S. PATENT DOCUMENTS

| | | | |
|---|---|---|---|
| 2,763,694 | 9/1956 | Buchner et al. | 568/451 |
| 2,880,241 | 3/1959 | Hughes | 568/591 |
| 4,388,477 | 6/1983 | Cooper | 568/451 |

*Primary Examiner*—Werren B. Lone
*Attorney, Agent, or Firm*—Donald W. Spurrell; J. Frederick Thomsen

[57] ABSTRACT

A hydroformylation process for producing relatively low ratios of normal to branched aldehyde product, wherein olefin having from 2 to 20 carbons, preferably 3–10 carbons, and most preferably one or more of ethylene, propylene and 1-butene is contacted in a reaction zone at a temperature of from about 60° C. to about 250° C., preferably from about 150° C. to about 200° C., and a pressure of from about 750 psig to about 10,000 psig, preferably from about 3,000 psig to about 4,000 psig, with hydrogen and carbon monoxide, in the presence of a catalyst containing from about $10^{-6}$ to about $10^{-3}$, preferably from about $5 \times 10^{-5}$ to about $5 \times 10^{-4}$, and most preferably from about $1.5 \times 10^{-4}$ to about $2.6 \times 10^{-4}$ moles of osmium per mole of said olefin and also containing cobalt, and molar ratio of Os/Co being from about 1/10 to about 1,000/1, preferably from about 1/1 to about 20/1, and most preferably from about 5/1 to about 15/1, for a sufficient period of time to permit reaction of said olefin with said hydrogen and carbon monoxide to form aldehyde product.

8 Claims, No Drawings

HYDROFORMYLATION PROCESS EMPLOYING UNMODIFIED OSMIUM-COBALT CATALYST

DESCRIPTION

This invention relates to the preparation of oxygenated organic compounds such as aldehydes by the reaction of carbon monoxide and hydrogen with an olefinic compound in the presence of a novel, osmium and cobalt containing catalyst. The aldehydes can be used as such or converted to useful alcohols or acids by known methods. More specifically the invention concerns such catalysts containing a major proportion of osmium and which produce low linear to branched aldehyde ratios, e.g., 0.8 to 1.6 when using propylene. In these catalyst, ligands such as triphenylphosphine, trialkylphosphines, mixed alkylarylphosphines, and the like are not employed and thus the term "unmodified" is used to describe the present catalysts.

Heretofore, oxo processes and catalysts have been tailored to the production of relatively high ratios of normal to branched aldehyde product, and the catalyst, reactants, and reaction conditions have been selected to give these ratios. See, for example, U.S. Pat. Nos. 3,527,809; 3,917,661; 3,965,192; and 4,148,830. In such processes the catalyst is typically cobalt or rhodium complexed with carbonyl, phosphines, phosphites and the like.

A principal objective of the present invention is to provide a catalyst system which gives a relatively low normal to branched aldehyde product ratio in high yield and at low catalyst concentrations.

This and other objectives hereinafter appearing have been attained in accordance with the present invention through the discovery that the combination of unmodified osmium and cobalt in certain proportions as the catalyst, in relatively low concentrations and under pressures of from about 750 to about 10,000 psig, in the hydroformylation of olefins, will produce unexpectedly low molar ratios of normal to branched aledhydes at production rates substantially exceeding that attainable with either of the individual metals as catalyst.

It is noted that the oxo activity of cobalt at the concentrations utilized herein is insignificant. Under the conditions of the present invention the oxo activity of the osmium catalyst alone is fairly high and produces butyraldehydes with a linear to branched ratio of 0.8 to 1.1. The present combination of osmium and cobalt, however, gives a similarly low ratio but at a significantly higher oxo activity. Moreover, with the present catalysts the linear to branched aldehyde ratio can be altered readily by adjustment of the osmium to cobalt molar ratio, and a selectivity to aldehyde product of about 99 percent has been obtained.

The present catalyst metals are charged to the pressure reactor, e.g. autoclave, in soluble form such as their salts of the type $OsX_n$ and $CoX_n$ where X is a radical (anion) derived from an inorganic or organic acid and n is 1–4 representing various valence or complexing states of the metals. Typically X is halogen, CO, or the anions of the acetylacetonate, acetate, propionate, butyrate, or naphthenate salts, or combinations thereof. For practical purposes it is more desirable that the catalyst metals be charged as salts of the acids derived from the particular product aldehydes, e.g., osmium isobutyrate and cobalt isobutyrate.

A wide range of catalyst concentrations may be used and are given herein as moles of Os or Co per mole of olefin feed. This term "mole" as used herein means gram mole. The osmium molar concentration ranges from about $10^{-6}$ to about $10^{-3}$, preferably $5 \times 10^{-5}$ to $5 \times 10^{-4}$, and most preferably, from about $1.5 \times 10^{-4}$ to about $2.6 \times 10^{-4}$. A wide range of osmium to cobalt molar ratios can be used for the purpose of this invention. A molar ratio of from about 1/10 to about 1,000/1 can be used with a preferred range being from about 1/1 to about 20/1, and the most preferred range being from about 5/1 to about 15/1.

The present invention, therefore, in its more preferred embodiments is defined as a hydroformylation process comprising contacting olefin having from 2 to 20 carbons, preferably 3–10 carbons, and most preferably one or more of ethylene, propylene and 1-butene in a reaction zone at a temperature of from about 60° C. to about 250° C., preferably from about 150° C. to about 200° C., and a pressure of from about 750 psig to about 10,000 psig, preferably from about 3,000 psig to about 4,000 psig, with hydrogen and carbon monoxide, in the presence of a catalyst containing from about $5 \times 10^{-5}$ to about $5 \times 10^{-4}$, preferably from about $1.5 \times 10^{-4}$ to about $2.6 \times 10^{-4}$ moles of osmium per mole of said olefin and also containing cobalt, the molar ratio of Os/Co being from about 1/10 to about 1,000/1, preferably from about 1/1 to about 20/1, and most preferably from about 5/1 to about 15/1, for a sufficient period of time to permit reaction of said olefin with said hydrogen and carbon monoxide to form aldehyde product.

It is particularly noted that the salts or carbonyl complexes of Os and Co may be considered as precursors to the active catalytic species which are derived therefrom in the reactor. Inherent in the process, however, is that the present salts or complexes are fed to the reactor as such and the olefin, $H_2$ and CO come into contact with each other in the presence thereof even though the aforesaid catalytic species forms therefrom.

In the case of propylene feed, the most preferred reaction conditions are temperatures of from about 150° C. to about 190° C., pressures of from about 3,000 psig to about 3,800 psig, and an osmium concentration of from about $1.5 \times 10^{-4}$ to about $2.6 \times 10^{-4}$ moles per mole of propylene. It is noted that in continuous hydroformylations the catalyst feed (recycle or make-up) may be continuously or periodically adjusted to maintain the desired Os and Co concentrations and molar ratios in the reaction zone.

In carrying out the hydroformylation in known continuous manner, conventional oxo equipment and procedures may be employed, such as an overflow reaction, the catalyst leaving the reaction zone with the product aldehyde, the product solution then passed through a series of vapor liquid separators, the gases being recycled to the reactor, and the liquid let down to atmospheric pressure by conventional techniques. This liquid comprising a mixture of aldehyde products, solvent, and catalyst may then be passed through a distillation column to remove aldehydes overhead, and the catalyst with high boiling base effluent recycled back to the reactor through suitable pressure pumping means.

In the continuous process, the syn gas ($H_2$+CO) is introduced into the reactor in a continuous manner by means, for example, of a primary compressor, and the ratio of hydrogen to carbon monoxide in the feed may be selected according to the particular olefin being hydroformylated and the selected reaction conditions, as is well known in the art. Generally, the molar ratio of hydrogen to carbon monoxide in the reactor is maintained within the range of above about 0.5 to about 4.0, but it has been found in many hydroformylations that the rate of reaction as well as yield of the desired product may be increased by increasing the hydrogen to carbon monoxide molar ratio to above 4.0, and even up to about 10.0 or more. The molar ratio of syn gas (total moles of $N_2+CO$) to olefin typically is maintained in the reaction zone at from about 0.5 to about 20, and preferably from about 1.2 to about 6.

The olefin is fed to the reactor by means of suitable pumps capable of operating under substantial pressures and the feed rates of the olefin and syn gas are selected to maintain the above-recited molar ratios of these reactants in the reactor. Typical useful olefins contain from 2 to 20 carbon atoms and preferably from 3 to 10 carbon atoms, straight-chain or branched-chain, and optionally containing groups or substituents which do not interfere with the hydroformylation process. Such olefins are ethylene, propylene, 1-butene, 2-methyl propylene, 2-methyl-1-butene, 1-pentene, 1-hexene, 1-heptene, 1-octene, 2-ethyl-1-hexene, 1-dodecene and 1-octadecene. Also useful in the present process are the internal olefins such as butene-2 and cyclic olefins such as cyclooctene. If desired, mixtures of olefins can be fed to the reactor.

Any suitable solvent which does not adversely affect the process and which is inert with respect to the catalyst, olefin, syn gas and the hydroformylation products may be used. Inert solvents of this nature are well known in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents include , 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the distillation column. The ratio of olefin to solvent can vary widely, but preferably is maintained within the range of 1/1 to 10/1 by liquid-volume.

The present osmium and cobalt mixed metal catalyst offers the advantages of being highly active for the oxo reaction at low concentrations, avoiding the need for expensive complexing agents such as triphenylphosphine or the like, achieving a desired linear to branched aldehyde ratio by suitable choice of the osmium to cobalt molar ratio, and giving high selectivity to desired oxo aldehydes product.

The invention is further illustrated by the following examples although it will be undertood that these examples are included merely for purposes of illustration and are not intended to limit the scope of the invention.

EXAMPLE 1

Preparation of the Osmium Tri-Isobutyrate and Cobalt Di-Isobutyrate Catalyst

Osmium trichloride (2.35 grams, $8\times10^{-3}$ moles) was admixed with sodium hydroxide (3.2 grams, $8\times10^{-2}$ moles) and isobutyric acid (7.0 grams, $8\times10^{-2}$ moles) in 60 ml of water. The solution was refluxed for one hour, cooled, and filtered. The solid catalyst was washed three times with 50 ml of water and dried. The cobalt di-isobutyrate catalyst was prepared in a similar fashion.

EXAMPLES 2-5

These Examples demonstrate the activity of the osmium tri-isobutyrate catalyst for the conversion of propylene to butyraldehydes (HBu).

In each example, propylene (1 mole) was placed in a 300 ml high-pressure reactor (autoclave) which contained 100 ml of toluene and $2.1\times10^{-4}$ moles of osmium as its tri-isobutyric acid salt. A 1/1 mole mixture of carbon monoxide and hydrogen was fed into the reactor to attain the designated pressure and the temperature increased as prescribed. These conditions were held for the 0.5 hr. hydroformylation period. The reaction yield and selectivity were determined by standard glc analysis.

| Ex. No. | Reaction Conditions | | | HBu Prodn Rate, lb/ft$^3$-hr | HBu N/Iso Ratio |
|---|---|---|---|---|---|
| | Temp, °C. | Press., psig | Time, hr | | |
| 2 | 150 | 2,500 | 0.5 | 6.93 | 0.92 |
| 3 | 180 | 2,500 | 0.5 | 5.02 | 0.88 |
| 4 | 150 | 3,500 | 0.5 | 7.2 | 1.03 |
| 5 | 180 | 3,500 | 0.5 | 18.4 | 1.02 |

EXAMPLE 6

This example demonstrates that at the low cobalt concentrations utilized within the scope of this invention the cobalt catalyst has only minor activity in the absence of osmium. The experimental procedure of above Example 5 was followed except that $3.4\times10^{-5}$ moles of cobalt as its di-isobutyric acid salt was used rather than the osmium salt. A butyraldehyde production rate of only 3.6 pounds per cubic foot-hour was attained.

EXAMPLES 7 and 8

These examples as compared to Examples 5 and 6 illustrate that under similar conditions the present osmium and cobalt mixed metal catalyst yields a reaction rate superior to either the osmium or the cobalt catalyst.

| | Example No. 7 | Example No. 8 |
|---|---|---|
| Os, Moles | $2.1\times10^{-4}$ | $2.1\times10^{-4}$ |
| Cobalt, moles | $1.7\times10^{-5}$ | $3.4\times10^{-5}$ |
| Molar Ratio Os/Co | 12.4/1 | 6.2/1 |
| Propylene, moles | 1 | 1 |
| Toluene, ml | 100 | 100 |
| Reaction Conditions | | |
| CO/H$_2$, mole ratio | 1 | 1 |
| Temperature, °C. | 180 | 180 |
| Pressure, psig | 3,500 | 3,500 |
| Time, hr | 0.5 | 0.5 |
| Production Rate, lb/ft$^3$-hr (HBu) | 21.4 | 31.27 |
| (HBu) N/Iso Ratio | 1.2 | 1.34 |

EXAMPLES 9 THROUGH 11

These examples illustrate the effect of varying the osmium to cobalt mole ratio using a constant $3.4\times10^{-5}$ moles of cobalt on the linear to branched HBu ratio under the same reaction conditions as Examples 7 and 8 above.

| Example No. | Os/Co Mole Ratio | HBu N/Iso Ratio |
|---|---|---|
| 9 | 1/1 | 1.43 |
| 10 | 5/1 | 1.54 |
| 11 | 10/1 | 1.34 |

The invention has been describe in detail with particular reference to preferred embodiments thereof, but it will be understood that variations and modifications will be effected within the spirit and scope of the invention.

I claim:

1. The hydroformylation process for producing relatively low normal/branched aldehydes comprising contacting olefin having from 2 to 20 carbons in a reaction zone at a temperature of from about 60° C. to about 250° C. and a pressure of from about 750 psig to about 10,000 psig with hydrogen and carbon monoxide in the presence of a catalyst containing from $10^{-6}$ to about $10^{-3}$ moles of osmium per mole of said olefin and also containing cobalt, the molar ratio of Os/Co being from about 1/10 to about 1,000/1, for a sufficient period of time to permit reaction of said olefin with said hydrogen and carbon monoxide to form aldehyde product.

2. The process of claim 1 wherein the catalyst contains from about $5\times10^{-3}$ to about $5\times10^{-4}$ moles of osmium per mole of olefin, and the molar ratio of Os/Co is from about 1/1 to about 20/1.

3. The process of claims 1 or 2 wherein said olefin is one or more of ethylene, propylene or 1-butene.

4. The process of claim 2 wherein said olefin is one or more of ethylene, propylene or 1-butene, and the reaction temperature is from about 150° C. to about 200° C.

5. The process of claim 4 wherein the molar ratio of Os/Co is from about 5/1 to about 15/1.

6. The process of claims 1, 2, 4 or 5 wherein the Os and Co are added to the reactor as their salts of the type OsXn and CoXn where X is the anion of an inorganic or organic acid and n is 1-4.

7. The process of claims 1, 2, 4 or 5 wherein the reaction is carried out at a pressure of from about 3,000 to about 4,000 psig.

8. The process of claim 1 wherein the olefin is propylene, the Os concentration is from about $1.5\times10^{-4}$ to about $2.6\times10^{-4}$ moles of osmium per mole of said olefin, the molar ratio of Os to Co is from about 5/1 to about 15/1, CO/$H_2$ molar ratio is from about 0.5 to about 4.0, the reaction temperature is from about 150° C. to about 190° C., and the reaction pressure is from about 3000 to about 3800 psig.

* * * * *